United States Patent [19]
Urbas et al.

[11] Patent Number: 5,724,030
[45] Date of Patent: Mar. 3, 1998

[54] SYSTEM MONITORING REPROGRAMMABLE IMPLANTABLE TRANSPONDER

[75] Inventors: Donald J. Urbas, Evergreen; David Ellwood, Lakewood, both of Colo.

[73] Assignee: Bio Medic Data Systems, Inc., Seaford, Del.

[21] Appl. No.: 322,644

[22] Filed: Oct. 13, 1994

[51] Int. Cl.⁶ .................................................. G08C 19/12
[52] U.S. Cl. .................. 340/870.17; 340/870.18; 340/870.31; 340/825.54; 455/38.3
[58] Field of Search .............. 340/870.17, 870.16, 340/870.18, 870.3, 870.31, 870.32, 825.54; 455/38.3, 41

[56] References Cited

U.S. PATENT DOCUMENTS

| | | | |
|---|---|---|---|
| 5,073,781 | 12/1991 | Stickelbrocks | 342/51 |
| 5,231,273 | 7/1993 | Caswell et al. | 455/38.3 |
| 5,252,962 | 10/1993 | Urbas et al. | 340/870.17 |
| 5,345,231 | 9/1994 | Koo et al. | 340/870.31 |

FOREIGN PATENT DOCUMENTS

| | | |
|---|---|---|
| 2 224 183 | 4/1990 | United Kingdom. |
| 2 258 589 | 2/1993 | United Kingdom. |

*Primary Examiner*—Jeffery Hofsass
*Assistant Examiner*—Andrew Hill
*Attorney, Agent, or Firm*—Stroock & Stroock & Lavan LLP

[57] ABSTRACT

A passive transponder including an antenna for receiving an input signal and transmitting an output and a memory for storing the data received by the transponder from an interrogator. The transponder can operate in either a read mode or a programming mode. The transponder includes an integrity circuit for indicating the integrity of the input signal, a monitoring circuit that monitors a characteristic of a host and an impedance modulator that prevents the overmodulation of the output signal.

26 Claims, 10 Drawing Sheets

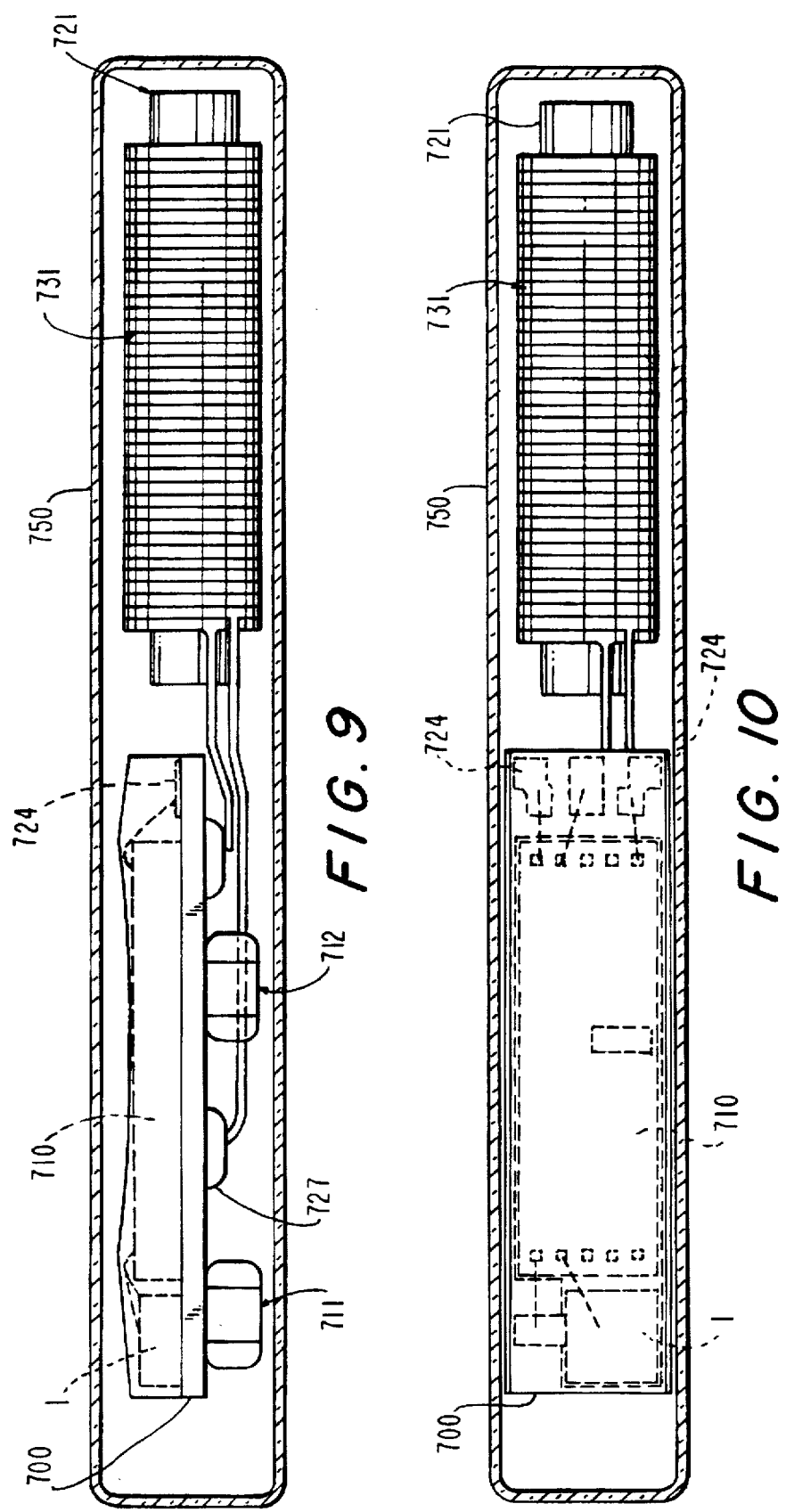

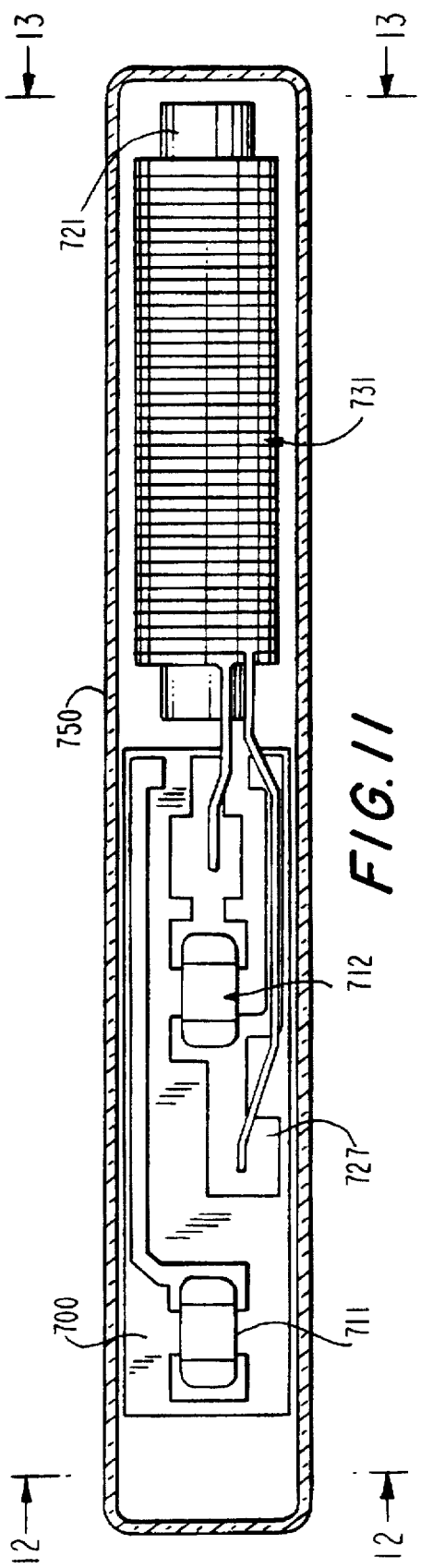
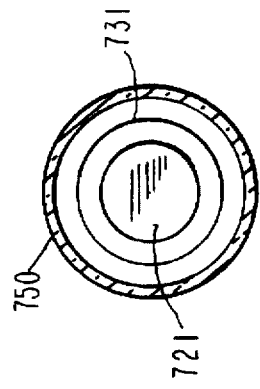
FIG. 13
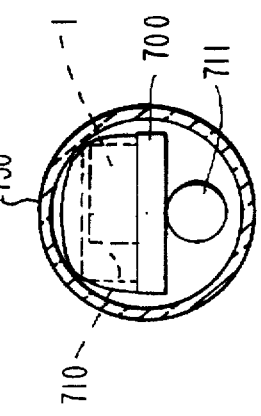
FIG. 12
FIG. 11
FIG. 14

SYSTEM MONITORING REPROGRAMMABLE IMPLANTABLE TRANSPONDER

BACKGROUND OF THE INVENTION

This invention is directed to a passive transponder, and, in particular to a passive transponder which is reprogrammable after completion of manufacture (and insertion in the host) and is utilized for monitoring characteristics of the host to which it is imbedded, and more in particular for identifying an animal and its characteristics.

Transponders and scanner systems are well known in the art. These systems include an interrogator which transmits and receives signals from a passive transponder. One such use is a transponder implanted in an animal. U.S. Pat. No. 5,252,962 describes a one time programmable EEPROM that can store an identification code that corresponds to the identification of the animal in which it is imbedded. It is also known in the art to reprogram a transponder utilizing an EEPROM or the like. However, the prior art transponders have been less than completely satisfactory because they provide little or no information to the interrogator to ensure proper programming. Accordingly, in a contemplated use such as animal identification, transponders have been unable to reliably indicate to the interrogator that the data is being properly stored, changed or deleted within each transponder.

Also, heretofore transponders have had circuitry designed to measure the temperature of the animal in which it is implanted. One such analog circuit described in U.S. Pat. No. 5,252,962 has been less than accurate. Therefore, it is desirable to provide a passive transponder which overcomes the shortcomings of the prior art, indicates to an interrogator whether sufficient power is being received in order to be programmed, senses an environmental condition, such as the temperature of the host animal, transmits this information along with other host information to an interrogator and can perform an essentially simultaneous exchange of information with the interrogator.

SUMMARY OF THE INVENTION

Generally speaking, in accordance with the instant invention, a passive transponder is provided, the transponder including an antenna for receiving an input signal to power the transponder, the signal also containing data and commands from the signal source and being also capable of transmitting an output signal to the signal source. The transponder also includes memory for storing data received by the transponder from the signal source, the transponder operating in either a READ mode for outputting information from the transponder to the signal source, or in a PROGRAMMING mode wherein the memory stores data in response to information contained in the input signal. The transponder also includes an integrity circuit for indicating to the signal source that sufficient power is available from the signal source for causing the memory to store the data. The transponder also includes a monitoring circuit for monitoring a characteristic of a host. The memory includes a plurality of memory storage locations, with locations addressed sequentially to read data stored in the memory and with addressing occurring at a rate which is a submultiple of the signal source frequency. The monitoring circuit monitors the characteristic during the period of time required to address a predetermined number of the addresses of the memory. The transponder also includes an impedance modulator for permitting substantially simultaneous two way communication between the transponder and signal source.

Accordingly, it is an object of the instant invention to provide an improved passive transponder.

A further object of the invention is to provide a passive transponder which senses and transmits the characteristic of an object into which it has been imbedded.

Another object of the invention is to provide a reprogrammable passive transponder capable of providing information to the interrogator to indicate that sufficient power is being received to program the transponder.

Yet another object of the instant invention is to provide an improved passive transponder for more accurately determining and communicating the temperature of a host.

A further object of the invention is to use phase modulation to more accurately transmit data to the interrogator.

Still another object of the invention is to utilize an impedance modulator to allow for essentially simultaneous transmission and reception of data with the interrogator having a passive design.

Another object of the invention is to improve circuit efficiency by utilizing common circuits to perform different functions in both read and program modes.

Yet another object of the invention is to provide a transponder which collects host characteristic data while reading data from the memory.

Another object of the invention is to improve circuit efficiency and performance by using a clock frequency and timing signals derived from, and locked to, the frequency of the signal source.

Another object of the invention is to improve data transmission rates by accomplishing measurement of host characteristics during transmission of stored information.

Another object of the invention is to provide circuitry to prevent inadvertent over-writing of any portion of the stored data.

Another object of the invention is to provide circuitry to provide selective over-writing of stored data.

Another object of the invention is to provide circuitry requiring a coded command to enter the program mode and thus prevent false programming.

Still other objects and advantages of the invention will in part be obvious and will in part be apparent from the specification.

The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 9 is a side elevation view of a passive transponder constructed in accordance with the instant invention;

FIG. 10 is a top plan view of a passive transponder constructed in accordance with the instant invention;

FIG. 11 is a bottom plan view of a passive transponder constructed in accordance with the instant invention;

FIG. 12 is a cross-sectional view taken along line 12—12 of FIG. 11;

FIG. 13 is a cross-sectional view taken along line 13—13 of FIG. 11; and

FIG. 14 is a block circuit diagram of an interrogator and passive transponder in accordance with the present invention.

DETAILED DESCRIPTION OF THE PREFERRED EMBODIMENTS

Figure 1:
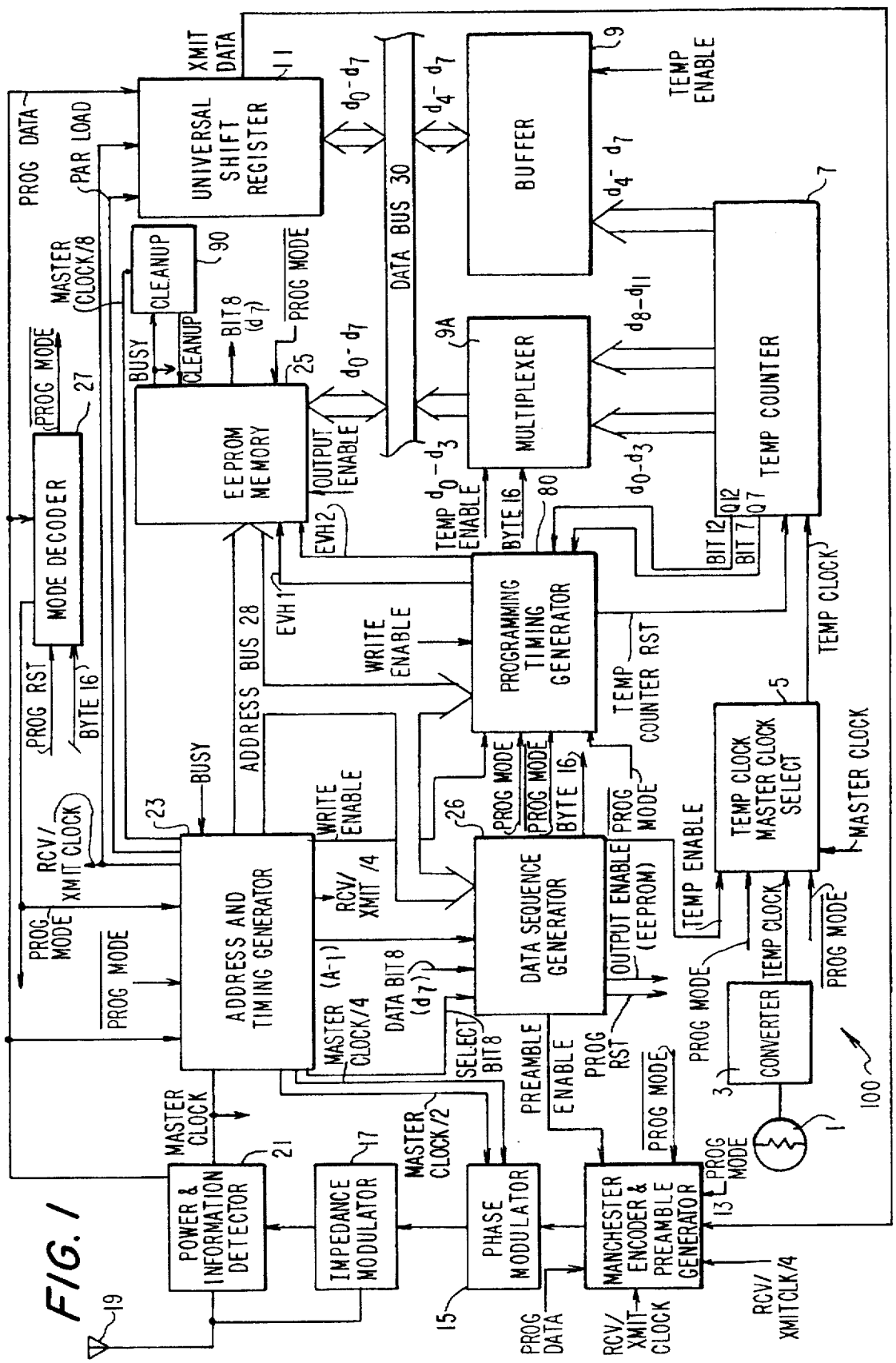
FIG. 1 is a block circuit diagram of a passive transponder constructed in accordance with a preferred embodiment of the instant invention.

Reference is first made to FIG. 1 in which a block diagram of an implantable passive transponder ("transponder"), generally indicated as 100, is provided. Transponder 100 may be placed, for example, under the skin of a laboratory animal, such as a rodent. In an exemplary embodiment, transponder 100 communicates with an interrogator 1000, as shown in FIG. 14, through inductive coupling generally known in the art from U.S. Pat. No. 4,730,198, which patent is incorporated herein by reference as if fully set forth herein. Interrogator 1000 includes the structures as disclosed in application Ser. No. 07/605,049, filed Oct. 29, 1990, which is incorporated as if fully set forth herein. A signal at a selected frequency is received from the interrogator by single coil antenna 19. This frequency is the MASTER CLOCK frequency for the transponder. In the exemplary embodiment described herein the MASTER CLOCK frequency is about 364 Khz. The waveform of the signal source can also contain data and control information to be sent to the transponder.

Transponder 100 will remain in the OFF state, until a signal of a sufficient power level is received by transponder 100 from the interrogator. The interrogator, which may be a handheld device, may also contain an adjustable exciter that controls, along with the distance between the interrogator and the transponder, the signal level to the transponder. When the interrogator transmits a signal of sufficient power to transponder 100, the transponder is placed in an "ON" state and can transmit data to, or receive data from, the interrogator. As will be explained in detail below, receipt and storage of data is only possible after the transponder has returned to the interrogator a signal indicating the transponder 100 has received a signal of sufficient voltage level to permit storage of data and the interrogator has responded with a command to enter the program mode. As will also be explained below, transponder 100 transmits data to an interrogator in a READ mode and receives and stores data from the interrogator in the PROGRAM mode.

To facilitate an understanding of FIG. 1, transponder 100 is initially described after transponder 100 has been programmed and after a user selected identification code has been stored in an electrically erasable programmable read only memory 25 ("EEPROM 25").

With reference to FIG. 1, a single antenna 19 is provided for both communication with, and receiving power from, the interrogator. Upon receipt of a signal of suitable power level, transponder 100 turns ON and enters the read mode and transmits data to the interrogator. The signal from antenna 19 is fed to a power and information detection circuit 21. The power and information detection circuit includes a full wave bridge rectifier. Detector 21 provides dc power for transponder 100, detects the envelope of the signal from which is established the PROG DATA signal, and generates the MASTER CLOCK signal by squaring up a half wave rectified portion of the signal received by antenna 19. Detection circuit 21 also includes the necessary overvoltage protection and level references needed for proper operation of the transponder. The PROG DATA signal is applied to a mode decoder circuit 27. Depending on the data, carried by the PROG DATA signal the transponder will remain in the READ mode or will be placed in the PROGRAM mode by outputting the associated PROG MODE and $\overline{\text{PROG MODE}}$ signals.

An address and timing generator 23, including dividers 70a, 70b (FIG. 2), receives the 364 KHz MASTER CLOCK signal from the power and information detection circuit 21 and through dividers 70a and 70b and associated logic gates, develops a number of timing and address signals: The TRANSMIT CLOCK and RECEIVE CLOCK signals are developed in divider 70a and both are fed to MUX 70 where MUX 70 selects, based on the status of the PROG MODE and $\overline{\text{PROG MODE}}$ lines, either the TRANSMIT CLOCK or the RECEIVE CLOCK for input to divider 70b as well as input to other blocks via the RCV/XMIT clock line, MASTER CLOCK divided by 2 and MASTER CLOCK divided by 4 signals are also developed in divider 70a and are used to develop 91 KHz signal in phase and a 91 KHz out of phase (90 degrees out of phase) to be used by phase modulator 15 for encoding data to be transmitted back to the interrogator. The $A_0$–$A_3$ outputs of divider 70b, whose input is either the RECEIVE CLOCK or the TRANSMIT CLOCK, is used to sequentially addresses the bytes of EEPROM 25 via address bus 28. The bit address signals $A_{-1}$ through $A_{-3}$ signals are also outputs of divider 70b and are used to identify the first and eighth bit of each byte and the period of time when the first 4 bits of the data stored in byte 15 of EEPROM 25 could be transmitted but are in fact replaced with a preamble.

Reference is again made to FIG. 1 wherein universal shift register 11 is depicted. Shift register 11 receives data from a data bus 30 for output during the READ mode. Address and timing generator 23 applies a PAR LOAD signal to shift register 11. When the PAR LOAD signal is high and the TRANSMIT CLOCK signal transitions from a low to high state during the first bit of every eight bit sequence; either stored data from EEPROM 25 or temperature data (described below) via buffer 9 or data multiplexer 9a is placed on data bus 30. During the READ mode, shift register 11 serially outputs the data to a preamble generator and Manchester encoder and preamble generator 13 ("encoder and preamble generator 13"). Encoder and preamble generator 13, in response to a PROG DATA signal, TRANSMIT CLOCK signal, and a divided TRANSMIT CLOCK signal, encodes the serial data received from shift register 11, generates a preamble and outputs the preamble and Manchester encoded data to phase modulator 15.

Phase modulator 15, using the MASTER CLOCK/2 signal and MASTER CLOCK/4 signal from address and timing generator 23 generates an in phase signal and out of phase signal necessary to encode the data appearing on the transmit data line. Phase encoding occurs in phase modulator 15 as the data on the line selects, via a multiplexer 55 (FIG. 6), the appropriate in phase or out of phase signal. Phase modulator 15 outputs the phase encoded data to impedance modulator 17.

Impedance modulator 17 modulates the apparent impedance of antenna 19 by selectively placing a load resistance across the antenna, at timing intervals that are determined by the signal received from antenna 19 and the phase modulated, Manchester encoded data. The changing load impedance across antenna 19 is what is sensed by the interrogator as the receive signal.

A thermistor 1 changes its resistance in response to temperature. A converter 3, controlled by thermistor 1, provides an output signal TEMP FREQ. The frequency of TEMP FREQ signal from temperature to frequency converter 3 ("converter 3") is a function of the temperature sensed by thermistor 1. A temperature clock-master clock selector 5, receives as a first input a TEMP ENABLE signal from a data sequence generator 26, either a PROG MODE signal a MASTER CLOCK signal and a TEMP FREQ signal. Selector 5 selects which of these signals will be upheld binary counter 7. In an exemplary embodiment, In the READ mode, counter 7 counts the positive going transitions in the TEMPCLOCK signal produced at the output of converter 3 (TEMP FREQ) during the timing interval the first 14 bytes from the EEPROM are being transmitted to the interrogator. As noted above, buffer 9 and data multiplexer 9a selectively couple the temperature data in counter 7 to data bus 30. Also as noted, the temperature data on data bus 30 is parallel loaded into shift register 11 and then serially outputted to Manchester encoder and preamble generator 13.

Data sequence generator 26 establishes when in the transmit cycle of the READ mode the information stored in EEPROM 25 (via the OUTPUT ENABLE signal), the preamble ( via the PREAMBLE ENABLE signal) and the temperature (via the TEMP ENABLE signal) are transmitted to the interrogator. The TEMP ENABLE signal controls the input to the temperature counter 7 when not in the PROGRAM mode via the temp clock-master clock selector 5. Data sequence generator 26 also identifies byte 16 (via the BYTE 16 signal) to allow the circuitry of mode decoder 27 to look for the command sequence that places the transponder in the program mode and provides the PROG RST signal that permits mode decoder 27 to look for the command sequence only if data bit 8 of the 16th byte stored in EEPROM 25 is not a zero.

The PREAMBLE ENABLE signal input to encoder and preamble generator 13 permits encoder 13 to apply a non-Manchester encoded preamble signal which indicates both transponder timing and the whether the voltage level on the PROG DATA line is above or below approximately 3 volts, i.e., sufficient to program transponder 100. Provided that transponder 100 is receiving sufficient power to remain ON, it remains in the READ mode unless and until it is placed in the PROGRAM mode. A predetermined pulse sequence on the PROG DATA line will place transponder 100 in the PROGRAM mode but this sequence should not be sent from the interrogator unless the transponder has notified the interrogator that the signal power level is adequate for programming EEPROM 25. The PROG DATA line is fed to mode decoder circuit 27 which decodes the sequence to determine if the command to enter the program mode has been received.

In the PROGRAM mode, data from the interrogator appears on the PROG DATA line, is clocked into the universal shift register 11 using the RECEIVE CLOCK signal, and then output parallel outputs, and therefor onto the data bus 30 and the input/output lines (d0–d7) of EEPROM 25. The clock signal of universal shift register 11 is the signal on the RCV/XMIT line and, is selected by MUX 70 (FIG. 2) when transponder 100 is in the PROGRAM mode. Once the eight bits of data are on data bus 30, address and timing generator 23 outputs a WRITE ENABLE signal to Programming Timing Generator 80.

Figure 2:
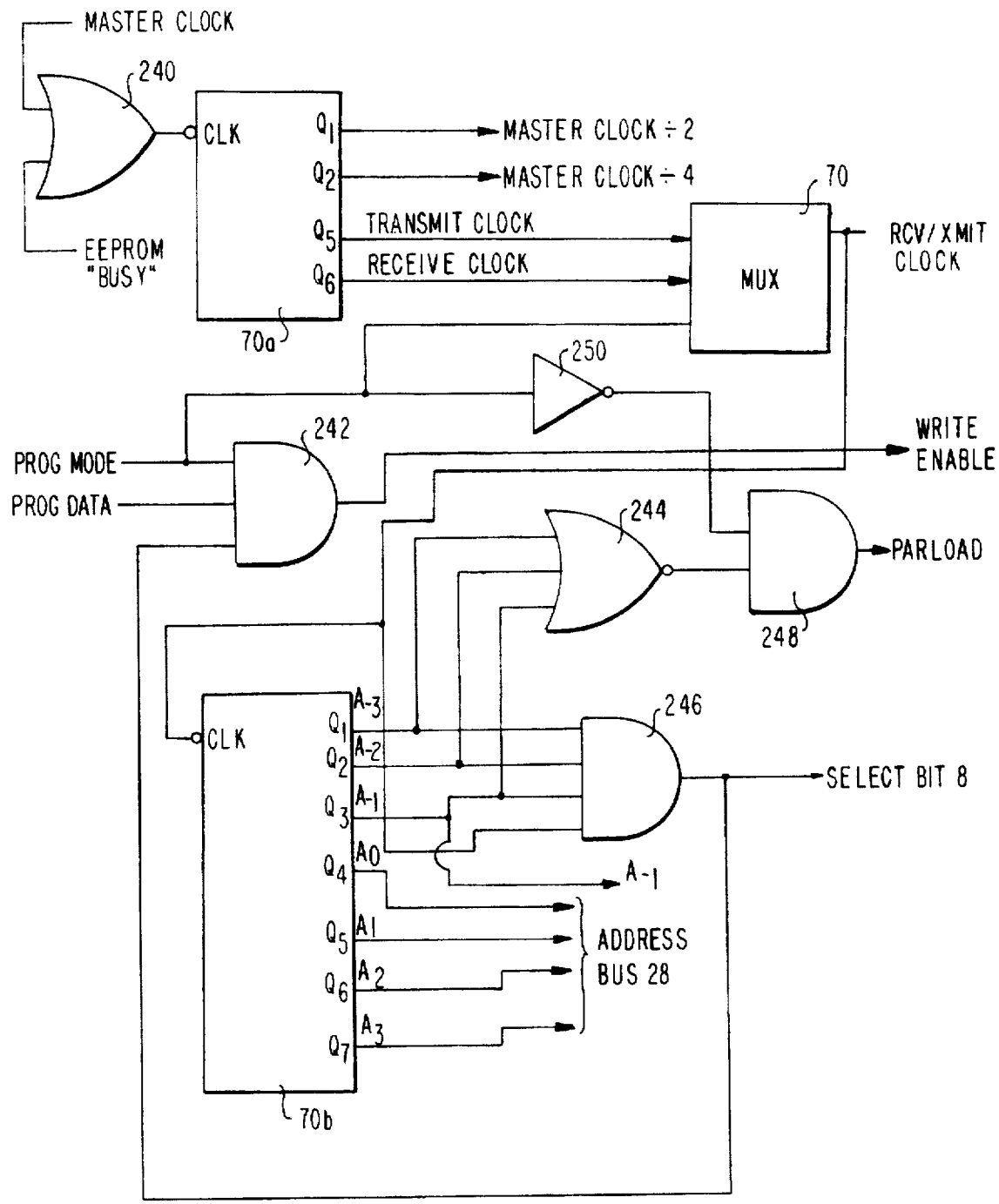
FIG. 2 is a block circuit diagram of an address and timing generator constructed in accordance with the invention.

Programming-timing generator 80, in response to the WRITE ENABLE signal, provides signals to EEPROM 25 to control the timing of the write cycles therein. During the write cycle, the busy output of EEPROM 25 disables divider 70a of address and timing generator 23 by removing the MASTER CLOCK input thus stopping the RECEIVE CLOCK and therefor preventing the EEPROM address from changing. Also during the write cycle, the temperature clock-master clock selector 5, which is also receiving the MASTER CLOCK and the TEMP FREQ, selects the MASTER CLOCK for input to counter 7 which provides the timing functions for the writing of data into EEPROM 25. After each byte is written to EEPROM 25, a clean-up circuit 90 is provided to enable EEPROM 25 to receive a subsequent byte of data in response to the MASTER CLOCK and a Busy signal from EEPROM 25 (FIG. 2).

Read Mode

When transponder 100 is "powered up", it defaults to the READ mode. Accordingly, immediately upon receiving sufficient power, and while transponder 100 is in the READ mode, transponder 100 will transmit three distinct types of data: the temperature of the animal in which the transponder is embedded; data stored in EEPROM 25, usually identification data for the animal; and a preamble that indicates the voltage level received by the transponder 100 and sets up a timing reference for the interrogator. The transmission of this data (preamble, temperature data, identification data) by transponder 100 is continually repeated as long as the signal transmitted by the interrogator provides sufficient power to the transponder and a command to enter the PROGRAM mode is not sent from the interrogator.

In a preferred embodiment, the preamble is followed by the temperature data and thereafter followed by the identification data stored in EEPROM 25. The temperature data contains information conveying the body temperature of the animal in which the transponder is embedded. Thereafter, and until the transponder is placed in the program mode or insufficient power is received by the transponder, the entire data stream will be continuously repeated.

Reference is again made to FIG. 2 to specifically describe the circuitry of transponder 100 for transmitting the above-mentioned data to the interrogator. Providing the various clock signals is the function of address and timing generator 23. Address and timing generator 23 includes an OR gate 240 which receives the 364 KHz MASTER CLOCK signal from power and information detection circuit 21 and a BUSY signal from EEPROM 25 and in the absence of a Busy Signal outputs the MASTER CLOCK to divider 70a. Dividers 70a and 70b and MUX 70, develop a number of timing and address signals: The TRANSMIT CLOCK and RECEIVE CLOCK signals are developed in divider 70a and both are fed to MUX 70 where MUX 70 selects either the TRANSMIT CLOCK or the RECEIVE CLOCK for input to divider 70b as well as input to other blocks in response to PROG MODE. MASTER CLOCK/2 and MASTER CLOCK/4 signals are also developed in divider 70a and are used to develop a first 91 KHZ signal, and a second 91 KHZ, 90 degrees out of phase with the first signal phase modulator 15 for encoding data to be transmitted back to the interrogator. The $A_0$–$A_3$ outputs of divider 70b, whose input is either the RECEIVE CLOCK signal or the TRANSMIT CLOCK signal, is used to sequentially address the bytes of EEPROM 25 via address bus 28.

Address and timing generator 23 also includes an AND gate 24b receiving the $A_{-0}$, $A_{-2}$, and signals on the RCV/XMIT line as inputs and produces a Select Bit 8 signal. An AND gate 242 receives PROG MODE, PROG DATA and Select Bit 8 signals as inputs and produces an WRITE ENABLE signal. An AND gate 244 receives the $A_1$–$A_{-3}$ signals as inputs and produces a Bit 1 signal. An AND gate 248 receives an inverted PROG MODE signal and the Bit 1 signal produces the PAR LOAD signal. As a result, the bit address signals $A_{-1}$ through $A_{-3}$ signals and the output signals of divider 70b are used to identify the first and eighth bit of each byte. The appropriate clock is selected by MUX 70 based on the status of the $\overline{\text{PROG MODE}}$ and not PROG MODE signals.

With reference to FIG. 1, EEPROM 25 preferably has 16 addressable bytes, each being addressable by address and timing generator 23 via address bus 28, specifically, output signals and $A_0$–$A_3$ the four high order bits of divider 70b. The OUTPUT ENABLE produced by data sequence generator 26 goes high permitting EEPROM 25 to output its data, and when low tri-states the output of EEPROM 25 so as not to conflict with data from buffer 9 and mutliplexer 9A. In the preferred embodiment, address and timing generator 23 sequentially addresses the addresses of EEPROM 25. As each address of EEPROM 25 is addressed in the READ mode, the data stored at that address is output onto data bus 30 and shifted out to the encoder and preamble generator 13. The loading of the data into shift register 11 will next be described.

At the end of 8 clock pulses of the MASTER CLOCK, the data on bus 30 is parallel loaded into shift register 11 when the high level on the PAR LOAD signal line from address and timing generator 23 is clocked into universal shift register 11 by a low to high transition of the TRANSMIT CLOCK appearing on the RCV/XMIT signal line from address and timing generator 23. Thereafter the data in shift register 11 is outputted serially to encoder and preamble generator 13 at the TRANSMIT CLOCK rate of ≈11 Khz (MASTER CLOCK/32).

The PREAMBLE ENABLE signal output of data sequence generator 26 indicates when the first half of data byte 15 could be transmitted, and forces encoder and preamble generator 13 to insert the 4 bits of the preamble into the serial data stream instead. The preamble both sets up a timing reference and indicates the voltage level of the received signal. The preamble and the circuitry necessary to insert the preamble into the data stream will now be described.

Figure 8:
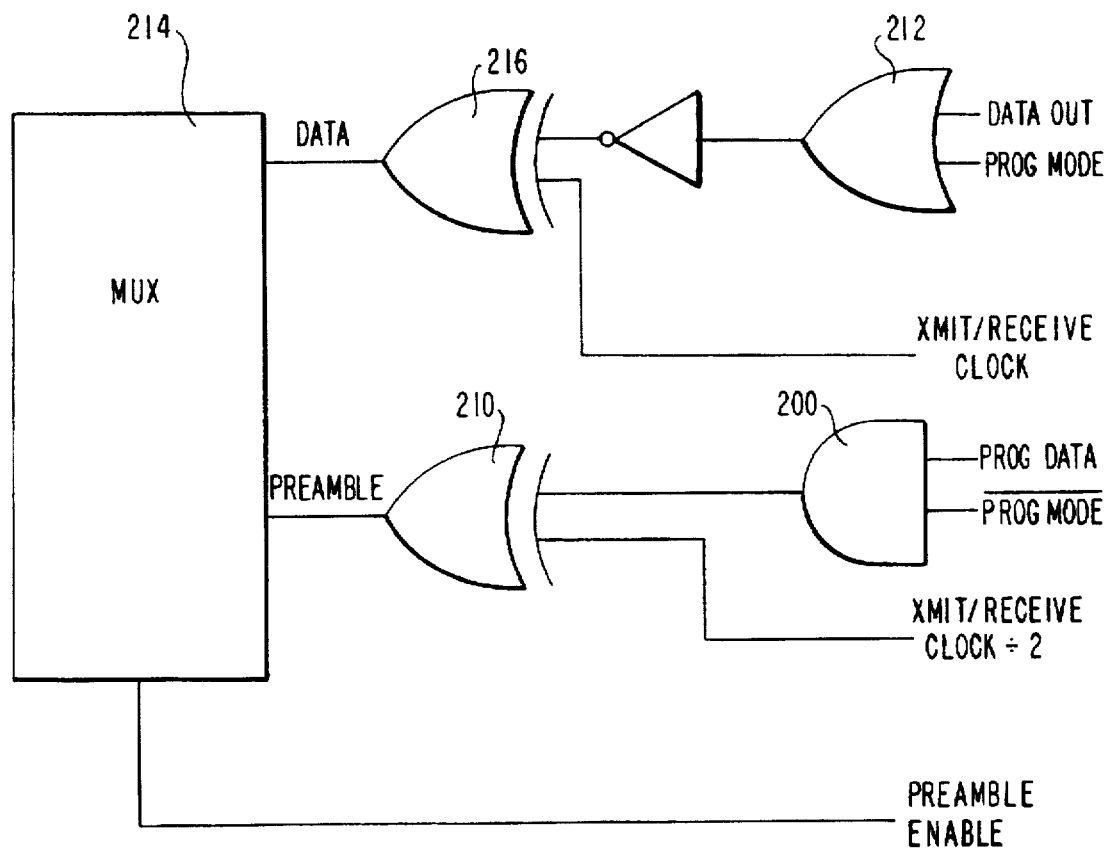
FIG. 8 is a circuit diagram of a Manchester encoder and preamble generator in accordance with the present invention.

Referring to FIG. 8, the preamble is readily detectable by the interrogator since, although it is processed in a manner similar to that used by the actual data, the exclusive OR gate 210 (FIG. 8) uses a clock rate of one half that used for the actual data and samples the output of gate 200 (FIG. 8) which is actually the PROG DATA line and this line indicates the signal level received by transponder 100. Specifically, the preamble portion remains in one state for two cycles of the TRANSMIT CLOCK and then remains in the opposite state for another two clock cycles.

Although preamble generators and Manchester encoders are well known in the art, by way of background, Manchester encoder and preamble generator 13 converts the serial data into positive or negative going transitions depending upon the logic level of the data being encoded. Whether the preamble begins in a transition to a high state or a transition to a low state depends on whether the signal received by the transponder exceeds approximately 3 volts.

The generation of the preamble will now be described in detail with further reference to FIG. 8. Encoder and preamble generator 13 includes an OR gate 212, receiving the DATA (from shift register 11) and PROG MODE signals as inputs. An EXCLUSIVE OR gate 216 receives the inverted output of OR gate 212 as a first input and the signal on the RCV/XMIT line as its other input and outputs a gated DATA signal to MUX 214. An AND gate 200 receives the PROG DATA signal and $\overline{\text{PROG MODE}}$ signal and provides a first input signal to EXCLUSIVE OR gate 210. EXCLUSIVE OR gate 210 receives the TRANSMIT CLOCK/2 as its second input and outputs the PREAMBLE to MUX 214. MUX 214 also receives the PREAMBLE ENABLE signal.

The $A_{-2}$ signal output by sequence divider 23 is a signal that is low for the first quarter (two clock cycles) and high for the second quarter of the time period during which an individual address of EEPROM 25 is addressed. Furthermore, when PROG DATA is low, the output of EXCLUSIVE OR gate 210 is low for two cycles of the $A_{-2}$ signal and then high for two cycles of the $A_{-2}$ signal. Conversely, when PROG DATA is high, occurring when the supply voltage from the interrogator is greater than approximately three volts, the preamble, output by XOR gate 210, is high for two clock cycles of the $A_{-2}$ signal and then low for two clock cycles of the $A_{-2}$ signal. Therefore, when the supply voltage of transponder 100 is less than approximately three volts, the preamble starts low and goes high. When the transponder supply voltage is greater than approximately three volts, the preamble starts high and goes low. In this way transponder 100 communicates the supply voltage to the interrogator so that the interrogator can determine whether the signal level at the transponder 100 is high enough for the transponder to enter the PROGRAM mode.

The combination of OR gate 212 and EXCLUSIVE OR gate 216 generates, as the output of XOR gate 216, a Manchester encoded data stream. MUX 214 selects between the Manchester encoded data and the preamble in response to the PREAMBLE ENABLE control signal. When the PREAMBLE ENABLE signal is low, one of the first fourteen bytes of data from EEPROM 25 is being outputted by shift register 11, i.e. the output of XOR gate 216. When PREAMBLE ENABLE signal is high, all fourteen bytes of data have been outputted from shift register 11 and the PREAMBLE SIGNAL, the output of XOR 210 is inputted to MUX 214.

Figure 4:
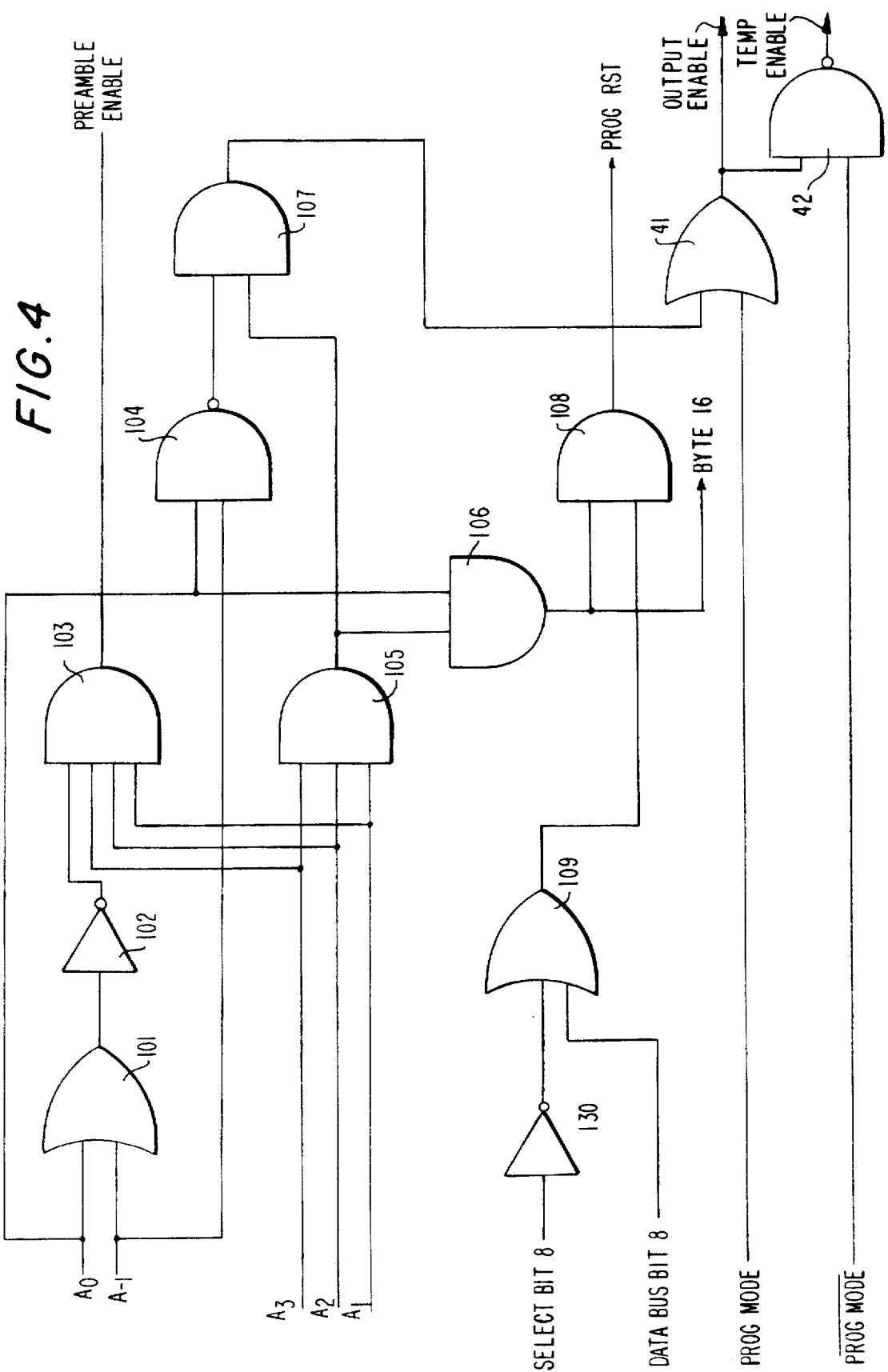
FIG. 4 is a circuit diagram of a data sequence generator constructed in accordance with the instant invention.

Reference is now made to FIG. 4 wherein the circuit of data sequence generator 26 for generating the PREAMBLE ENABLE signal is depicted in detail. Data sequence generator 26 decodes the address from address and timing generator 23 on address bus 28 and outputs the appropriate enable signals accordingly. Data sequence generator 26 includes an OR gate 101 which receives the $A_{-0}$ and $A_{-1}$ outputs of address and timing generator 23, as its two inputs and produces an input to an invertor 102. The output of invertor 102, which is low when all even bytes are addressed or when the last 4 data bits are being transmitted, provides a first output to an AND gate 103, AND gate 103 receiving $A_1$–$A_3$ as its remaining inputs which are high during bytes 15 and 16. The output of AND gate 103, the PREAMBLE ENABLE signal, is therefore only high during the first half of the fifteenth byte. AND gate 103 will generate the PREAMBLE ENABLE signal. Accordingly, in response thereto, MUX 214 will output the preamble.

Temperature Sensing

A chip thermistor 1 is provided to sense and produce information regarding the temperature of the animal. Chip thermistor 1 is a variable resistor, varying in resistance in response to changes in temperature. The combination of chip thermistor 1 and voltage to frequency converter 3 form a temperature to frequency converter whose output is a frequency (TEMP FREQ) signal in response to the resistance of chip thermistor 1 and hence the temperature of the animal in which the transponder is embedded. The TEMP FREQ signal is input to temp clock-master clock select 5 and outputted to counter 7 when the TEMP ENABLE signal is high and when the transponder 100 is not in the PROGRAMMING mode. Temp counter 7 counts the number of frequency cycles of the TEMP FREQ signal to obtain a digital number indicating the temperature being measured. The disabling of counter 7 in response to a low level on the TEMP ENABLE signal output by data sequence generator 26 to temperature clock-master clock selector 5 is discussed below. Counter 7 counts the number of oscillations of the TEMP FREQ signal occurring during the addressing of the first 14 bytes of EEPROM 25.

While in the READ mode and during the addressing of the fifteenth byte and the first half of the sixteenth byte of EEPROM 25, the TEMP ENABLE signal is low which prevents, by the action of temp clock-master clock select 5, the TEMP FREQ signal from being inputted to the counter 7. Generation of the TEMP ENABLE signal will now be described. Generation of the OUTPUT ENABLE signal of EEPROM 25, which is essentially the inverse of the TEMP ENABLE signal, will also be described.

Data sequence generator 26 includes a NAND gate 104 (FIG. 4) receiving $A_0$ and $A_{-1}$ as its inputs and whose output will therefore be low during the last half of the time when all even numbered bytes are addressed. Art AND gate 105 receives $A_1$–$A_3$ as its inputs so that its output, which is a first input to AND gate 107, is high during bytes 15 and 16. The output of NAND gate 104 is also input to AND gate 107 so that the output of AND gate 107 is high during the time interval of byte 15 and the first half of the time interval defined by byte 16. The output of AND gate 107 is fed to the input of OR gate 41 whose other input is the PROG MODE signal. The output of OR gate 41, which is the OUTPUT ENABLE, either follows the output of AND gate 107 or is held high in the PROGRAM mode. The OUTPUT ENABLE signal must be high during the PROG MODE to permit data to be stored in EEPROM 25 and low when data in the EEPROM is being read; during the reading of the first fourteen bytes of stored data and during byte 16 when bit 8 of byte 16 is checked to determine whether a logic 0 is stored there.

The output of OR gate 41 is, along with the $\overline{\text{PROG MODE}}$ signal the input to NAND gate 42 and the output of this NAND gate is the TEMP ENABLE signal. The TEMP ENABLE signal is therefore low during all of byte 15 and the first half of byte 16 and high during the time interval defined by the second half of byte 16.

Figure 3:
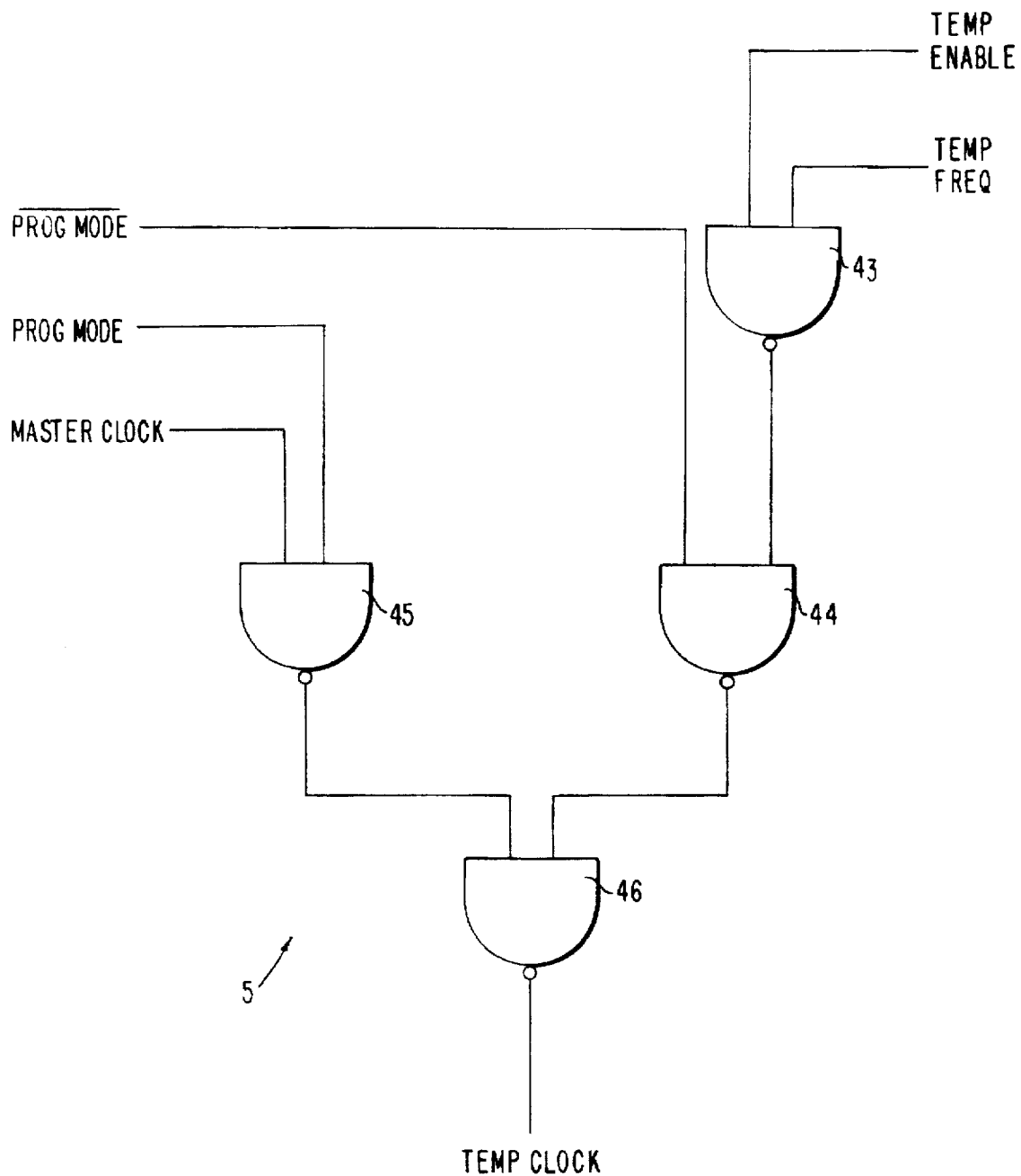
FIG. 3 is a circuit diagram of a temperature clock-master clock selector constructed in accordance with the instant invention.

Reference is now also made to FIG. 3 which illustrates the temp frequency-master clock selector 5 circuit in detail. A NAND gate 42 receives the $\overline{\text{PROG MODE}}$ and the output of OR gate 41 and provides the TEMP ENABLE signal as a first input to NAND gate 43. NAND gate 43 also receives the TEMP FREQ signal and outputs a signal to NAND gate 44. NAND gate 44 also receives the $\overline{\text{PROG MODE}}$ signal and outputs a signal to NAND gate 46. A NAND gate 45 receives the MASTER CLOCK and PROG MODE and outputs a signal to NAND gate 46 which outputs TEMP FREQ. After the fourteen bytes of data have been transmitted, the output of a NAND gate 42 (TEMP ENABLE), which is low during all of byte 15 and the first half of byte 16, disables the TEMP FREQ signal from being input to counter 7. Therefore, the TEMP FREQ signal will no longer appear at the input of NAND gate 44 and no further counting of the transitions of the TEMP CLOCK signal takes place. The output of counter 7 is placed on data bus 30 and then outputted as described below.

Buffer 9 is a tri-state buffer and multiplexer 9a is a 4 bit, 2 input multiplexer with tri-state outputs. During the second half of the period during which the fifteenth byte of EEPROM 25 is addressed, the most significant four bits of TEMP COUNTER 7 are placed on the data bus 30 by multiplexer 9, and then loaded into shift register 11 by the action of the PAR LOAD signal and the TRANSMIT CLOCK. During the period in which the sixteenth byte of EEPROM 25 would be addressed, the middle 4 bits of TEMP COUNTER 7 are placed on the data bus 30 by buffer 9 and the low order bits of TEMP COUNTER 7 are placed on the data bus 30 by multiplexer 9a. The lower 8 bits of the TEMP COUNTER which are now on data bus 30, are loaded into shift register 11 by the PAR LOAD signal and the TRANSMIT CLOCK. The data on data bus 30 is loaded into shift register 11 at the beginning of each byte. The temperature data is then serially shifted out of shift register 11 to encoder and preamble generator 13 at the transmit clock rate. After the data for byte 16 is latched into universal shift register 11 the temperature counter 7 is reset to 0 by the TEMP RST signal output by programming timing generator 80 so that it will be ready to start counting again at the beginning of the next cycle. Furthermore, in an exemplary embodiment, temperature counter 7 can also be reset in response to the POWER ON reset signal which resets each time the interrogator signal from antenna 19 first powers up transponder 100.

The output of Manchester encoder and preamble generator 13 (the data stream, including the EEPROM data, the non-Manchester encoded preamble and temperature data) is input to phase modulator 15 at a clock rate of 11 KHz (TRANSMIT CLOCK) selected by MUX 70 of the address and timing generator 23.

Figure 6:
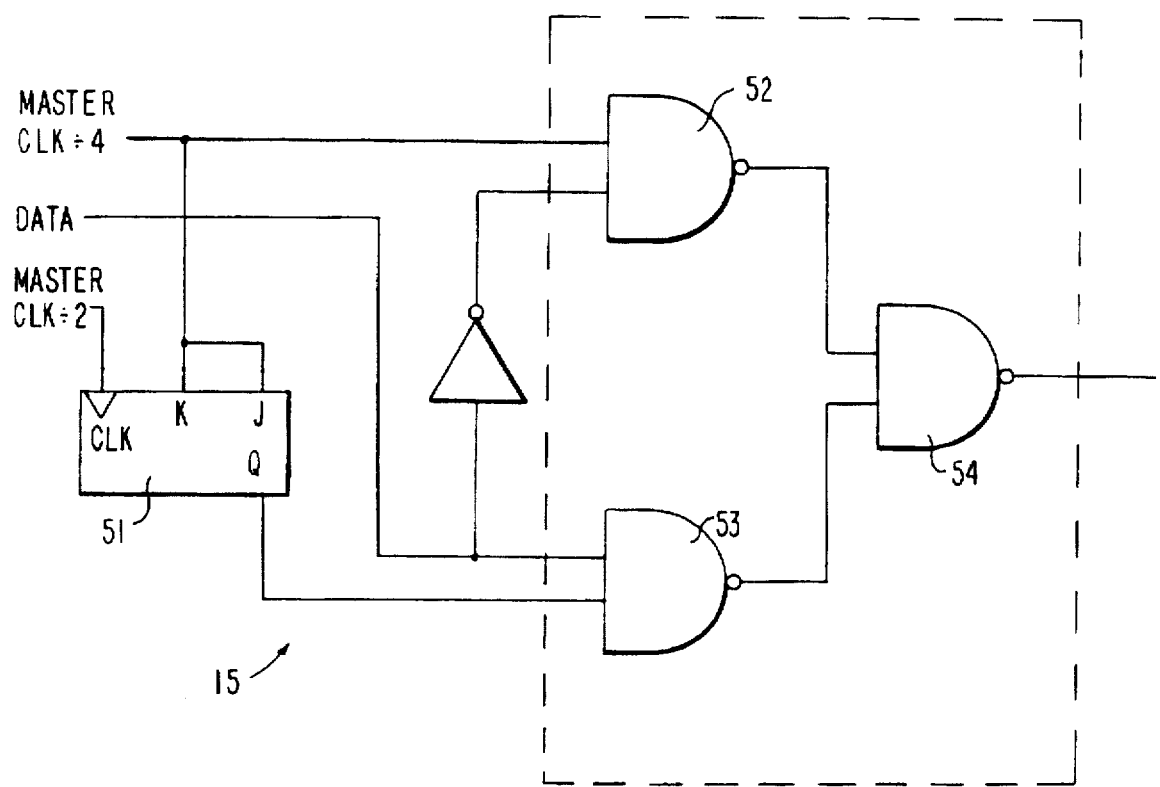
FIG. 6 is a circuit diagram of a phase modulator constructed in accordance with the instant invention.

Reference is next made to FIG. 6, wherein a circuit diagram of phase modulator 15 is provided. The MASTER CLOCK/2 and MASTER CLOCK/4 signals output from address and timing generator 23 are input to a phase modulator 15. A phase shifter 51 receives the MASTER CLOCK/2 signal and provides as its output, an out of phase PHASE CLOCK at 91 KHz that is 90° out of phase with the MASTER CLOCK/4 (the in phase PHASE CLOCK) outputted by address and timing generator 23. The 91 KHz unshifted PHASE CLOCK signal is input directly into NAND gate 52. A second input to NAND gate 52 is the output of an invertor 55 which inverts the output signal from the encoder and preamble generator 13. A second NAND gate 53 receives the 91 KHz signal out of phase, the PHASE CLOCK signal and the output of encoder 13. A NAND gate 54 receives the outputs of both NAND gates 52, 53 so that phase modulator 15 outputs either an in phase 91 KHz signal or an out of phase 91 KHz signal in response to the signal from the encoder and preamble generator 13 and provides an output to impedance modulator 17.

Impedance modulator 17 receives the output signal from phase modulator 15. Impedance modulator 17 prevents overmodulation on antenna 19 which could affect the proper reception of the 364 KHz clock signal which is being received by the interrogator. Impedance modulator 17 prevents impedance modulation from occurring when the voltage across the coil is too high.

Impedance modulator 17 affects the combined coil and load resistance impedance only during periods that will cause the least amount of disturbance to the MASTER CLOCK signal so that a large 91 KHz return signal is produced without interrupting the 364 KHz MASTER CLOCK signal.

Figure 7:
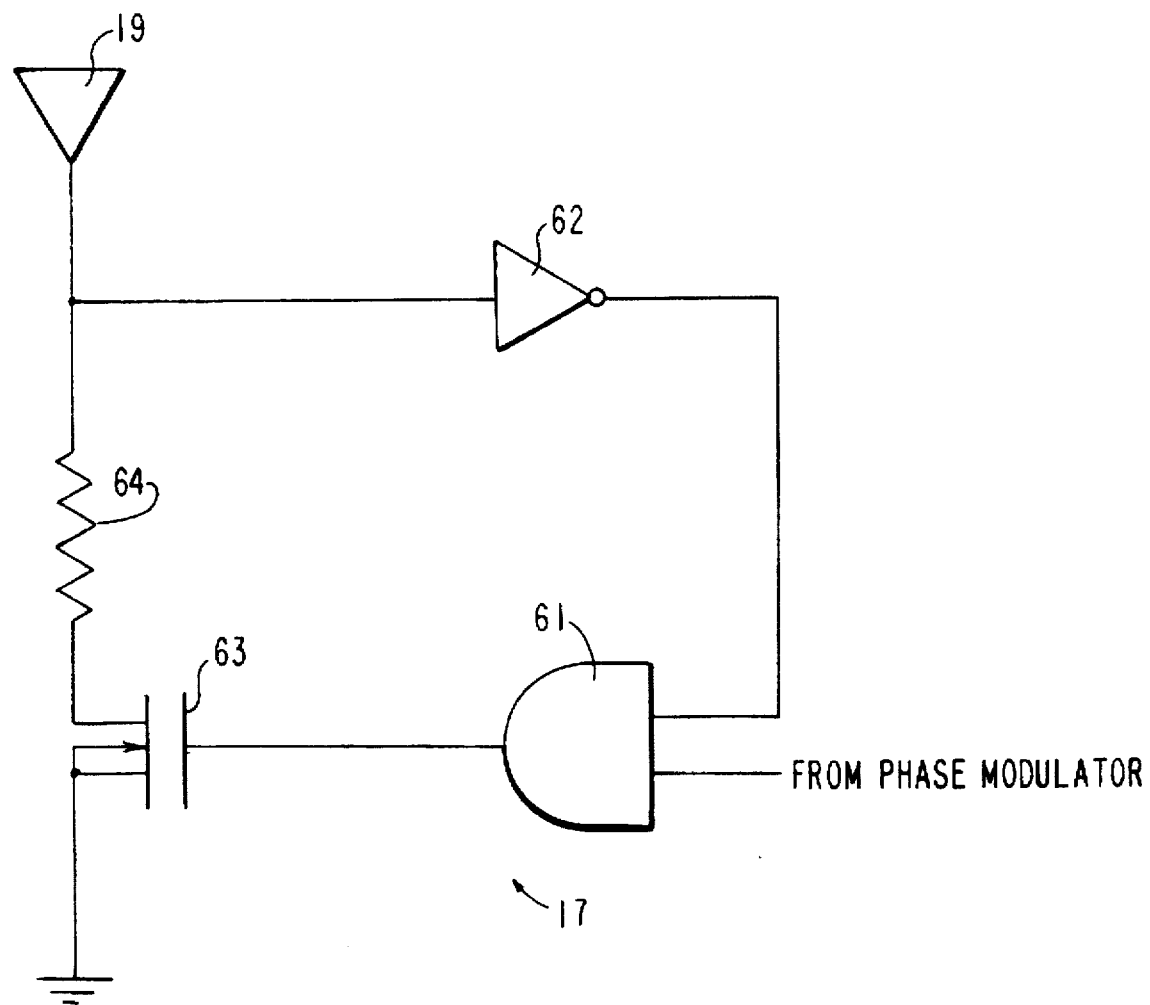
FIG. 7 is a circuit diagram of an impedance modulator constructed in accordance with the instant invention.

Reference is made to FIG. 7 where impedance modulator 17 is shown in detail. Impedance modulator 17 includes a MOSFET transistor 63, a resistor 64, a Schmidt trigger 62 providing a first input to AND gate 61. The output of phase modulator 15 provides the second input to AND gate 61. A high level output of AND gate turns on MOSFET 63.

When MOSFET 63 is turned ON, one side of the coil forming the antenna 19 is connected through resistor 64 to ground thereby loading antenna 19. When MOSFET 63 is turned OFF, resistor 64 does not load the coil. Switching the load resister 64 in and out of the antennae circuit modulates the apparent impedance of antenna 19. The changing impedance of the antenna is sensed at the interrogator as the receive signal carrier frequency of 91 KHz. The interrogator detects the phase encoded data by sensing the phase change of the carrier frequency. These phase transitions are sensed by the interrogator, and depending upon when, relative to the preamble transition the subsequent phase transitions occur, indicates to the interrogator whether the data is a one or a zero.

Impedance modulator 17 switches the load onto the circuit when the output of phase modulator 15 is high and the instantaneous voltage at the antenna 19 is less than the input high level threshold for inverter 62. If the voltage at antenna 19 is too high or the output of phase modulator 15 goes low, the load is disconnected from the antenna.

Programming Mode

The second mode in which transponder 100 may operate is the PROGRAM mode. Since Transponder 100 is in the READ mode by default, to enter the PROGRAM mode, the interrogator must sense that the voltage level on the PROG DATA line exceeds approximately 3 volts and then must transmit three pulses so that the voltage level of the PROG DATA signal transitions through a threshold voltage, of approximately 3 volts. This can be referred to as a "window of opportunity". In the preferred embodiment described herein, the voltage level is a function of the signal level output of the interrogator and the distance from the interrogator, and the "window of opportunity" is the time interval time when transponder 100 is transmitting the 16th byte of data (corresponding to the temperature). The state of the actual voltage on the PROG DATA line is communicated to the interrogator by the low to high or high to low transition at the middle of the preamble. The logic level of the preamble appears at the output level of EXCLUSIVE OR gate 210 (FIG. 9). Since the preamble is inserted into the data stream during the first half of the fifteenth byte and the preamble timing in this embodiment violates Manchester encoding timing in this embodiment, the interrogator can establish timing with the transponder.

The utilization of a deliberate signal at a predetermined transition point in the transponder timing cycle to place transponder 100 in the program mode assists in preventing noise on the PROG DATA line from placing transponder 100 in the PROGRAM mode.

If the voltage level at the PROG DATA output signal of transponder 100 is not at least approximately 3 volts, as indicated by the direction of transition at the middle of the preamble, the interrogator operator will realize that the signal output level of the interrogator must be increased or the interrogator must be moved closer to the transponder.

Figure 5:
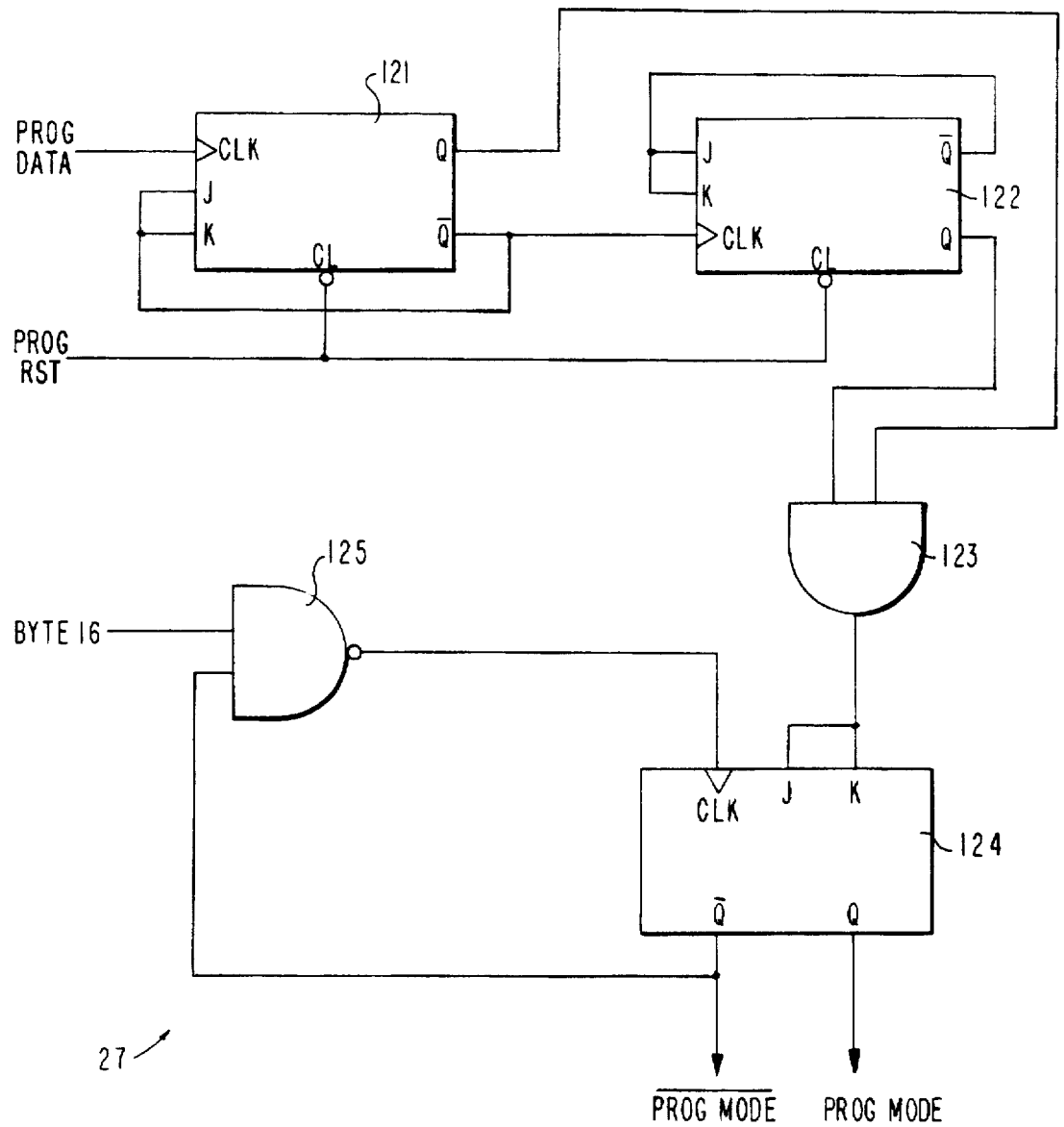
FIG. 5 is a circuit diagram of a mode decoder constructed in accordance with the instant invention.

Reference is next made to FIG. 5 wherein mode decoder 27 is described in greater detail. Assuming the transponder is receiving sufficient power, entry into the programming mode will occur if three pulses have been received during the time that byte 16 of EEPROM 25 is addressed, and bit 8 of byte 16 is not a logic low (or binary zero). The programming mode is indicated by a high level at the output of FLIP FLOP 124. Whether or not a high level appears at the output of FLIP FLOP 124 is determined by the output of AND GATE 123 when byte 16 is addressed at the end of the timing interval. The transponder will remain in the PROGRAM mode until power is removed therefrom.

A Select Bit 8 signal from address and timing generator 23 is inputted through inverter 130 to OR gate 109. The other input to OR gate 109 receives the output of the most significant bit of EEPROM 25 so that the output of OR gate 109 can only be a low if data bit 8 is low during the time bit 8 is being addressed (by the Select Bit 8 signal). An AND gate 108 receives the signal from OR gate 109 and from AND gate 106, which indicates that the 16th byte of EEPROM 25 is being addressed, and outputs a low level PROG RST signal to clear flip flop 122 if data bit 8 of byte 16 of EEPROM 25 is low or allows the PROG RST signal to remain high throughout the time interval of byte 16.

Assuming that the PROG RST line is high, which can only occur during the time byte 16 is being addressed, an input logic pulse on the PROG DATA line clocks a logic 1 onto the Q output of flip-flop 121. With the first pulse on the PROG DATA line, one input of AND gate 123 goes high. With the second pulse on the PROG DATA line, the $\overline{Q}$ output of flip-flop 121 goes high, causing the $\overline{Q}$ output of flip-flop 122 to latch a logic 1 thereon. Therefore, the second input of AND gate 123 goes high while the first input of AND gate 123 goes low. With the third pulse on the PROG DATA line, flip-flop 121 toggles once again and the Q output of flip-flop 121 becomes a logic 1. Because the Q output of flip-flop 121 goes high, flip-flop 122 does not toggle so the second input of AND gate 123 remains high, while the first input of AND gate 123 is also high, placing a logic high on the output of AND gate 123 which indicates that three pulses have occurred.

The output of AND gate 123 will remain a logic 1 providing that the PROG RST does not reset the flip flops prior to the end of the 16th byte.

The method by which clocking of flip flop 124 occurs is now described. NAND gate 125 (FIG. 5) receives, in addition to the high level indicating that the 16th byte is being addressed, the $\overline{\text{PROG MODE}}$ signal which is a logic high since the transponder is in the READ mode. Therefore, at the end of the 16th byte, the output of NAND gate 125 will change state from a low to a high and thus clock the state of the output of AND gate 123 into flip flop 124. Therefore, if the output AND gate 125 is low, either because 3 pulses were not received during byte 16 or a 0 was located in bit 8 of byte 16, mode decoder 27 maintains the transponder in the READ mode and if the output of AND gate 125 is high, mode decoder 27 places the transponder in a PROGRAMMING mode.

If however there is a logic low stored in bit 8 in the 16th byte of EEPROM 25, the output of AND gate 108 will remain low during the time bit eight of the 16th byte would be transmitted and this would clear the flip flops 121 and 122, bringing the output of AND gate 123 low. The low signal from gate 123 will be applied to flip flop 124 at the end of byte 16 and therefore prevent the transponder from entering the PROGRAMMING mode.

The method by which byte 16 is identified by Data sequence generator 26 will now be described. During the 15th and 16th bytes, address lines $A_1$–$A_3$ are all at a logic high, and the output of AND gate 105 is high and is inputted to AND gate 106 (FIG. 4). Since the other input to AND gate 106 is $A_0$, the output of AND gate 106 will be high only during byte 16's addressing time.

In the PROG MODE the RECEIVE CLOCK from sequence divider 23 is used to clock in data to register 11 and the temperature freqmaster clock selector 5 selects the MASTER CLOCK as the clock input to temperature counter 5.

During the PROGRAM mode the interrogator causes data to appear on PROG DATA by changing the amplitude of the received signal which causes the supply voltage of the transponder to move above or below approximately 3 volts. Also, as stated above, once the PROGRAM mode is initiated, shift register 11 starts shifting in data at the rate determined by the receive clock. The interrogator determines when to send each bit of data because the interrogator is receiving the transponders receive clock. Specifically, this is the clock input to EXCLUSIVE OR gate 216. The interrogator sends out the first bit of data, most significant bit first, and then waits for a positive transition of the RECEIVE CLOCK before sending the next bit. Once it receives a positive transition, the interrogator sends the next bit and this process is continued until the first byte of data has been sent.

After all eight bits of data have been shifted into the universal shift register 11 and put on the data bus, a logic high or low (which would be the ninth bit) is sent from the interrogator to indicate whether the prior eight bits are to be stored. If it desired to store the prior 8 bits a logic one is sent and if it is not desired that a particular address byte be programmed or reprogrammed, the interrogator transmits a logic zero. If a high is sent from the interrogator, indicating that it is desired to store the prior eight bits, the address and timing generator 23 outputs the WRITE ENABLE signal to the programming timing generator 80 and thus starts the write cycle. The development of the write enable signal is described as follows.

An AND gate 246 of address and timing generator 23 determines when the last half of bit eight is being received by sensing address lines $A_1$–$A_{-3}$ and the RECEIVE CLOCK. The output of AND gate 246 is fed to AND gate 242 which also has as its inputs, PROG DATA and PROG MODE signals. Accordingly, when all the inputs are high a WRITE ENABLE is generated.

WRITE ENABLE going high starts the write cycle timing sequence with timing for the writing cycle of EEPROM 25 established by the MASTER CLOCK and counter 7 in conjunction with the Q7 and Q12 outputs of counter 7. Logic levels on Q7 and Q12 are sensed within program and timing generator 80 to determine when a specific number of MASTER clock transitions are counted and therefore a specific time period has passed. Temp-clock-master clock selector 5 acts as a multiplexer selecting between the MASTER CLOCK or TEMP FREQ as an output. In response to a high signal on the PROG MODE line, the output of NAND gate 46 is the MASTER CLOCK.

When WRITE ENABLE goes high, the write cycle begins with EHV1 output of programming timing generator 80 being high and the EHV2 output of programming timing generator 80 being low for a period of 5.63 ms. (FIG. 1) When the EHV1 signal goes high EEPROM 25 begins the write cycle and outputs a high on the BUSY signal line keeping the output of OR gate 240 (of the address and timing generator 23) high and disabling the MASTER CLOCK signal input to divider 70a of address and timing generator 23. The MASTER CLOCK is disabled so that the addressed byte of EEPROM 25 does not change during the write cycle and the RECEIVE CLOCK being sent back to the interrogator, also does not change state. For the next 176 μs both EHV1 and EHV2 are low. Then for the next 5.63 ms the EHV2 is high and the EHV1 signal is low. When EHV1 is high EEPROM 25 is erasing the data in the byte that was being addressed at the time the MASTER CLOCK signal was disabled. The write cycle is 11.43 ms based on a master clock signal of 364 KHz.

Because the MASTER CLOCK has been disabled from address and timing generator 23, there are no timing signals being transmitted by address and timing generator 23 while data is being written into EEPROM 25. Accordingly, the RECEIVE CLOCK signal is not being transmitted by transponder 100. Accordingly, no RECEIVE CLOCK signal is detected by the interrogator and the interrogator is able to determine that the write cycle is being performed.

If the person programming the interrogator wishes to write into only that single byte, the interrogator must wait until it detects the receive clock again, indicating that the write cycle has been completed and then power the transponder down, removing transponder 100 from the PROGRAM mode. Transponder 100 may then be powered up again to verify the change because transponder 100 will enter the READ mode by default upon repowering. If the person programming transponder 100 wishes to write data into the next byte, the interrogator uses the RECEIVE CLOCK as a signal to transmit the next byte of data and then sends a logic one after the data and waits for transponder 100 to finish the next write cycle. Any address of EEPROM 25 may be written to in this manner. Bytes 15 and 16, although never output because the preamble and temperature are transmitted during the time the data in these address locations would otherwise be transmitted, may be accessed for programming. As previously noted, by writing a zero to the most significant bit of byte 16, the data within EEPROM 25 may be made permanent.

EEPROM 25 requires a CLEAN UP pulse after the data has been programmed therein so that EEPROM 25 is ready for the next write cycle. A CLEANUP circuit 90 outputs a clean-up pulse in response to both the BUSY SIGNAL of EEPROM 25 and the MASTER CLOCK/8 signal (FIGS. 1, 2). Furthermore, when the BUSY signal is brought low the MASTER CLOCK can pass to address and timing generator 23 and the next address location of EEPROM 25 will be addressed.

Reference is now made to FIGS. 9–12 in which a transponder 100 constructed in accordance with the instant invention is provided. Transponder 100 includes a substrate 700. A chip thermistor 1 is mounted on substrate 700. A chip 710 housing each of the structures including EEPROM 25 and Manchester encoder and preamble generator 13 is also supported upon substrate 700. Capacitors 711 and 712 are also mounted on the substrate. These capacitors were not included on the chip because the required capacitance was too large. Capacitor 712 is used to tune coil 731 to 364 KHz and capacitor 711 is used to filter the output of the on-chip full bridge rectifier. Chip 710, chip thermistor 1, capacitor 711 and capacitor 712 are electrically coupled to each other by connecting traces 727 deposited on substrate 700. Antenna 19 is formed about a ferrite rod 721. Antenna 19 is formed by wrapping a coil 731 about ferrite rod 721. Coil 731 is coupled to chip 710 and capacitor 712 through bonding pads 724.

In an exemplary embodiment, transponder 100 is encapsulated in a glass capsule 750. The capsule is no more than 0.600 inches and has a inner diameter between 0.068 and 0.072 inches and an outer diameter of between 0.082 and 0.086 inches. The glass capsule may either be coated with a protective epoxy, replaced entirely with a protective epoxy or treated to prevent migration in animals. Furthermore, a glass tube may be sealed using direct heat, flame or laser.

A passive transponder constructed and arranged as disclosed herein provides many advantages heretofore not obtainable. By providing a transponder which changes the preamble in response to the voltage level of an incoming signal, the transponder is able indicate to the interrogator whether sufficient power is being received in order to be programmed. By monitoring the addressing of the memory addresses and utilizing the time during which certain memories are addressed, the monitoring of the characteristic of the transponder is performed in a more accurate and efficient manner. By providing an impedance modulator coupled to the antenna coil, it is possible to exchange information with the signal source substantially simultaneously.

It will thus be seen that the objects set forth above, and those made apparent from the preceding description are efficiently obtained and, since certain changes may be made in the above construction without departing from the spirit and scope of the invention, it is intended that all matter contained in the above description or shown in the accompanying drawings shall be interpreted as illustrative and not in a limiting sense. It is also to be understood that the following claims are intended to cover all of the generic and specific features of the invention herein described and all statements of the scope of the invention which, as a matter of language, might be said to fall there between.

What is claimed is:

1. A passive transponder comprising:
   antenna means for receiving an input signal containing data from a signal source and transmitting an output signal to said signal source;
   memory means for storing said data received by said transponder from said signal source, said transponder being in one of a read mode for outputting said data to said signal source as said output signal and a programming mode wherein said memory means stores said data in response to said input signal; and
   integrity means for indicating to said signal source the sufficiency of said input signal for causing said memory means to store said data.

2. The passive transponder of claim 1, further comprising mode decoder means for determining the waveform of said input signal during a predetermined time period and causing said transponder to be in said programming mode if said waveform corresponds to a predetermined waveform.

3. The passive transponder of claim 1, wherein said integrity means modifies said output signal to indicate the sufficiency of said input signal.

4. The passive transponder of claim 1, wherein said output signal includes a preamble and integrity means changes the preamble to indicate the sufficiency of said input signal.

5. The passive transponder of claim 1, wherein said memory means is an EEPROM having a plurality of byte addresses therein, said EEPROM storing data during said programming mode by undergoing a write cycle, said data being written into an addressed byte of said EEPROM during said write cycle and further comprising indicating means coupled to said EEPROM and for providing an indication of the occurrence of said write cycle.

6. The passive transponder of claim 5, wherein said indicating means prevents an output signal from being transmitted to said signal source.

7. The passive transponder of claim 5, further comprising serial/parallel means for transmitting data serially from said memory means during said read mode and for transmitting data in parallel into said memory means during said programming mode.

8. The passive transponder of claim 7, further comprising a transmit clock that operates at a first frequency, said data being transmitted to said signal source at said first frequency during said read mode, and a receive clock that operates at a second frequency during said programming mode, said data received from said signal source being stored in said memory means at said second frequency, said first frequency being greater than said second frequency.

9. The passive transponder of claim 1, including program enable means for enabling said transponder to change from said read mode to said programming mode in response to said input signal.

10. The passive transponder of claim 1, further comprising monitoring means for monitoring a characteristic of a host.

11. The passive transponder of claim 10, wherein said characteristic is the temperature of said host.

12. The passive transponder of claim 10, wherein said monitoring means includes a chip thermistor, at least one counter, and at least one buffer.

13. The passive transponder of claim 1, including impedance modulation means for permitting said antenna means to output said output signal and receives said input signal substantially simultaneously by applying a load to said antenna means in response to said output signal to reduce interference with said input signal.

14. A system for monitoring a reprogrammable transponder, said system comprising:
   a passive transponder;
   an interrogator for transmitting an output signal containing data to said transponder and receiving an input signal from said transponder; and
   said transponder including antenna means for receiving said output signal containing said data from said interrogator and transmitting said input signal to said interrogator; memory means for storing said data received by said transponder from said interrogator, said transponder being in one of a read mode for outputting said data to said interrogator as said input signal and a programming mode wherein said memory means stores said data in response to said output signal from said interrogator; and integrity means for indicating to said interrogator the sufficiency of said output signal for causing said memory means to store said data.

15. A passive transponder comprising: antenna means for receiving an input signal containing data from a signal source and transmitting an output signal to said signal source;
   memory means for storing said data received by said transponder from said signal source, said transponder being in one of a read mode for outputting said data to said signal source as said output signal and a programming mode wherein said memory means stores said data in response to said input signal; and monitoring means for monitoring a characteristic of a host, wherein said monitoring means is coupled to said memory means, said memory means including a plurality of memory addresses, each of said plurality of addresses being sequentially addressed in response to said input signal, said monitoring means monitoring said characteristic during the period of time required to address a predetermined number of said addresses of said memory means and producing a characteristic measurement, said output signal including said characteristic measurement.

16. The passive transponder of claim 15, further comprising timing sequencer means for controlling at least one timing signal of said memory means and means for converting said monitoring means into clock means for providing a signal to said timing sequencer means.

17. The passive transponder of claim 15, including integrity means for indicating to said signal source the sufficiency of said input signal for causing said memory means to store said data.

18. The passive transponder of claim 15, including impedance modulation means for permitting said antenna means to output of said output signal and receive said input signal substantially by applying a load to said antenna means in response to said output signal to reduce interference with said input signal.

19. The passive transponder of claim 15, wherein said monitoring means includes a chip thermistor, at least one counter, and at least one buffer.

20. The passive transponder of claim 15, further comprising mode decoder means for determining the waveform of said input signal during a predetermined time period and causing said transponder to be in said programming mode if said waveform corresponds to a predetermined waveform.

21. A passive transponder comprising:

an antenna for receiving an input signal containing data from a signal source and transmitting an output signal to said signal source;

memory means for storing said data received by said transponder from said signal source, said transponder being in one of a read mode for outputting said data to said signal source as said output signal and a programming mode wherein said memory means stores said data in response to said input signal; and impedance modulation means for modulating the impedance of the antenna to output a carrier signal formed by the changing impedance permitting said antenna to output said output signal and receive said input signal substantially simultaneously by applying a load to said antenna in response to said output signal to reduce interference with said input signal, said impedance being modulated in response to the input signal.

22. The passive transponder of claim 21, including integrity means for indicating to said signal source the sufficiency of said input signal for causing said memory means to store said data.

23. The passive transponder of claim 22, further comprising mode decoder means for determining the waveform of said input signal during a predetermined time period and causing said transponder to be in said programming mode if said waveform corresponds to a predetermined waveform.

24. The passive transponder of claim 21, wherein said impedance modulation means includes a transistor in series with a resistor.

25. A system for monitoring a characteristic of a host, said system comprising:

a transponder;

an interrogator for transmitting an output signal containing data to said transponder and receiving an input signal from said transponder;

said transponder including antenna means for receiving said output signal containing data from said interrogator and transmitting said input signal to said interrogator; memory means for storing said data received by said transponder from said interrogator, said transponder being in one of a read mode for outputting said data to said interrogator as said input signal and a programming mode wherein said memory means stores said data in response to said output signal; and monitoring means for monitoring a characteristic of a host, wherein said monitoring means is coupled to said memory means, said memory means including a plurality of memory addresses, each of said plurality of addresses being sequentially addressed in response to said output signal, said monitoring means monitoring said characteristic during the period of time required to address a predetermined number of said addresses of said memory means and producing a characteristic measurement, said input signal including said characteristic measurement.

26. A system for monitoring a reprogrammable transponder, said system comprising:

a transponder;

an interrogator for transmitting an output signal containing data to said transponder and receiving an input signal from said transponder;

said transponder including art antenna for receiving said output signal containing data from said interrogator and transmitting said input signal to said interrogator; memory means for storing said data received by said transponder from said interrogator, said transponder being in one of a read mode for outputting said data to said interrogator as said input signal and a programming mode wherein said memory means stores said data in response to said output signal; and impedance modulation means for modulating the impedance of the antenna to output a carrier signal formed by the changing impedance permitting said antenna to output said input signal and receive said output signal substantially simultaneously by applying a load to said antenna in response to said input signal to reduce interference with said output signal, said impedance being modulated in response to the input signal.

\* \* \* \* \*